United States Patent [19]

Okuyama et al.

[11] Patent Number: 5,676,997
[45] Date of Patent: Oct. 14, 1997

[54] FORMATION OF CALCIUM PHOSPHATE COATING FILM AND PRODUCTION OF SUBSTITUTE FOR HARD TISSUE IN LIVING BODY

[75] Inventors: Masahiko Okuyama; Katsuya Yamagiwa, both of Aichi, Japan

[73] Assignee: NGK Spark Plug Co., Ltd., Nagoya, Japan

[21] Appl. No.: 531,862

[22] Filed: Sep. 21, 1995

[30] Foreign Application Priority Data

Sep. 21, 1994 [JP] Japan ................... 6-254235

[51] Int. Cl.$^6$ ................... A61K 6/033; B05D 3/02
[52] U.S. Cl. ................... 427/2.26; 427/2.29
[58] Field of Search ................... 427/2.27, 2.29, 427/2.26

[56] References Cited

U.S. PATENT DOCUMENTS

| | | | |
|---|---|---|---|
| 4,699,742 | 10/1987 | Nakamura et al. | 264/56 |
| 4,752,457 | 6/1988 | Toriyama et al. | 423/308 |
| 4,836,994 | 6/1989 | Inoue et al. | 423/308 |
| 4,911,953 | 3/1990 | Hosonuma et al. | 427/343 |
| 5,030,474 | 7/1991 | Saita et al. | 427/2.27 |
| 5,141,576 | 8/1992 | Shimamune et al. | 427/2.27 |
| 5,232,878 | 8/1993 | Kasuga et al. | 106/35 |
| 5,441,635 | 8/1995 | Ichitsuka et al. | 210/656 |
| 5,605,713 | 2/1997 | Boltong | 427/2.29 |

*Primary Examiner*—Diana Dudash
*Attorney, Agent, or Firm*—Sughrue, Mion, Zinn, Macpeak & Seas, PLLC

[57] ABSTRACT

A process for producing a high purity and dense calcium phosphate coating film with bioaffinity on a high strength base, such as a base for a substitute for a hard tissue in a living body, comprising (1) dissolving (a) a salt containing phosphorus, a salt containing calcium, and a chelating agent capable of coordinating to either one or both of the metallic ions of these salts or (b) a chelate compound containing at least one of phosphorus and calcium and a salt containing the other in a solvent to prepare a sediment-free coating solution, (2) coating a base with the coating solution, (3) drying the coated base, and (4) calcining the coated base.

8 Claims, No Drawings

FORMATION OF CALCIUM PHOSPHATE COATING FILM AND PRODUCTION OF SUBSTITUTE FOR HARD TISSUE IN LIVING BODY

FILED OF THE INVENTION

This invention relates to a process for forming a calcium phosphate coating film and a process for producing a substitute for hard tissue in a living body. More particularly, it relates to a process for forming a calcium phosphate coating film which can be suitably applied in the formation of a coating of a calcium phosphate compound on a ceramic or metallic base in the production of a substitute for hard tissue in a living body, such as artificial bones, artificial dental roots, and artificial joints.

BACKGROUND OF THE INVENTION

It is known that calcium phosphate compounds have excellent bioaffinity and sinters thereof are biological materials capable of chemically bonding to bones or substituting for bones. However, the mechanical characteristics of calcium phosphate compounds, such as strength, toughness and wear resistance, are not sufficient for use as a substitute for a hard tissue. On the other hand, alumina, zirconia, metallic titanium, and the like have excellent strength but biologically inactive. Therefore, it is expected that a high strength material, such as zirconia or alumina, with a biologically active calcium phosphate coating thereon would be a high strength material with biological activity.

Known means for forming a calcium phosphate compound coating on the surface of ceramics with high adhesion include plasma spray coating, sputtering, and glass fusion.

However, sputtering or plasma spray coating is difficult to apply to a base of complicated shape and expensive raw materials and an exclusive apparatus therefor are required. In particular, although plasma spray coating has been put to practical use, since it requires a high temperature such as several thousands to about 10,000° C., deterioration of the base and decomposition of the coating film occur, and the resulting film becomes porous. The problem associated with glass fusion is that the glass used for fusion between a base and a film remains as an impurity after fusion bonding reducing the bioaffinity of the film.

SUMMARY OF THE INVENTION

Accordingly, an object of the present invention is to provide a process for forming a highly pure and dense film of a calcium phosphate compound.

Another object of the present invention is to provide a process for producing a high purity material with excellent bioaffinity irrespective of shape.

The present invention relates to a process for producing a calcium phosphate coating film comprising (1) dissolving (a) a salt containing phosphorus (P), a salt containing calcium (Ca), and a chelating agent capable of coordinating either one or both of the metallic ions of these salts or (b) a chelate compound containing at least one of phosphorus and calcium and a salt containing the other in a solvent to prepare a sediment-free solution, (2) coating a base with the solution, (3) drying the coated base, and (4) calcining the dried coated base.

DETAILED DESCRIPTION OF THE INVENTION

The raw materials to be used for formation of a calcium phosphate coating film are a calcium salt, a phosphorus salt, and a chelating agent. An already prepared chelate compound of at least one of phosphorus and calcium may also be used as a raw material, if desired. For example, a chelate compound composed of a calcium ion bonded to a multidentate ligand may be used in place of a calcium salt and a chelating agent therefor. From the viewpoint of ease in operation and control and production cost, however, it is preferable to use inorganic or organic salts.

Various inorganic or organic calcium or phosphorus salts may be used with no particular limitation. Suitable inorganic salts include nitrates, chlorides, bromides, iodides, chlorates, chlorites, nitrites, and sulfites. Suitable organic salts which can be used include acetates, oxalates, lactates, tartrates, citrates, benzoates, isobutyrates, and maleates. In order to prepare a sediment-free solution, those salts which are sufficiently soluble in a reaction solvent (water or an organic solvent) are preferred because the coating operation can be performed at a high concentration. A carbonate or a sulfate is not preferred because of its slow reaction progress. Preferred examples of the salts for calcium include nitrates, chlorides, nitrites, acetates, oxalates and citrates. Preferred examples of the phosphorus salts include $(NH_4)_2HPO_4$ and $NH_4H_2PO_4$.

The chelating agent which can be used in the present invention is a multidentate ligand capable of coordinating with a metallic ion to form a chelate compound. Examples of suitable chelating agents are dimethyl glyoxime, dithizone, oxine, acetylacetone, glycine, ethylenediaminetetraacetic acid (EDTA), and nitrilotriacetic acid (NTA), with EDTA being particularly preferred due to its high solubility and reactivity. An example of the chelate compound containing at least one of phosphorus and calcium includes calcium ethylenediaminetetraacetic acid.

The Ca/P atomic ratio in the raw materials preferably ranges from 1.4 to 1.75. With a Ca/P ratio falling within this range, a hydroxyapatite phase having a Ca/P atomic ratio of 1.67 (hereinafter referred to as HAP) or a calcium tertiary phosphate phase having a Ca/P atomic ratio of 1.5 (hereinafter referred to as TCP) which have excellent bioaffinity can be formed on calcining at 600° to 1300° C. It is also possible to form an HAP-TCP mixed crystal phase by adjusting the Ca/P atomic ratio of the raw materials. The Ca/P atomic ratio in the raw materials more preferably ranges from 1.5 to 1.67, and is most preferably 1.67.

A sediment-free solution is prepared from the above-described raw materials, for example, as follows. Ammonium ethylenediaminetetraacetate (EDTA) is dissolved in water as a solvent, and calcium nitrate is added to the solution, followed by stirring thoroughly to conduct reaction. Then, ammonium phosphate is added thereto, followed by stirring thoroughly to conduct further reaction to prepare a clear, sediment-free coating solution. Should sediment remain in the solution, the coating film is no homogeneous. If a calcium salt and a phosphate salt are dissolved in a solvent without using a chelating agent, a precipitate is formed upon mixing, and a clear solution is not obtained. Therefore, a chelating agent is essential for assuring homogeneity of the coating film. The coating solution is taken as a sediment-free solution if it has no sediment and suspension and is a clear solution with visual observation. In preparing the coating solution, the solution may be heated at a boiling temperature of the solvent or lower in order to enhance the solubility, or may be refluxed at the boiling temperature or higher. Thus, the temperature in preparing the coating solution is not limited, but room temperature may be preferable.

The solvent for dissolving the starting material to prepare the sediment-free solution may be chosen from solvents which do not generate any sediment. For example, alcohols, ketones, aldehydes, ethers, carbon halides and hydrocarbons may be used. When EDTA is used, water is most generally used as the solvent.

The coating solution can be maintained in a solution state as long as its pH is kept at 4 or higher. If the pH of the solution is less than 4, there is a tendency for crystals to precipitate from the solution. The precipitate comprises EDTA, and it seems that the stability of the complex is reduced at a lower pH. This is the basis for limiting the pH value of the solution in a preferred embodiment of the present invention. The pH adjustment can be effected by addition of aqueous ammonia for shifting to an alkaline side or by addition of hydrochloric acid for shifting to an acidic side. Other acids or bases can be used if desired. In order to obtain a transparent gel film which does not cause deposition after coating or drying, the pH value of the coating solution is preferably from 4 to 6.

While a clear reaction solution containing Ca and P may be used as a coating solution as such, it is preferred to concentrate the solution so as to make the coating film denser and thicker. Concentration can be carried out by gradually removing the solvent by heating at a temperature of 100° to 150° C. or by heating at 40° to 90° C. under reduced pressure whereby the viscosity of the solution increases without forming a precipitate to provide a clear and viscous coating solution.

The molar concentration of the total metal (Ca+P) in the system for dissolving the raw material is preferably 0.2 mol/l or below. Where it is 0.25 mol/l or higher, a clear solution can be prepared, but the gel obtained by concentration tends to be less clear, with precipitation of crystals or turbidity on the surface occurring, which would be a cause of formation of an impurity phase in the steps of coating and drying. Such an adverse phenomenon does not occur as long as the total metal molar concentration is 0.20 mol/l or less. This is the basis for limiting the metal concentration of the solution as another preferred embodiment of the present invention.

Coating of a base with the thus prepared solution can be carried out by application, spraying, dip coating, spin coating, and the like. Examples of the base material include alumina, zirconia, titanium alloy (e.g., Ti-6Al-4V) and stainless. Coating at one time is preferably carried out so as to be a coating thickness of from 0.01 µm to several micrometers. If the coating solution is coated too thick, cracks may be caused in drying. The coating layer is then dried, generally in the air at a temperature of from room temperature to a boiling point of a solvent used, for example, at a temperature of from room temperature to 100° C. After drying, the coated base may be pre-fired at 500° C. or below to decompose an organic matter.

The coated base is calcined at a temperature of about 500° to 1300° C. whereupon a film of sintered calcium phosphate compound is formed on the surface of the base. As a result of the calcination, any organic matter is combusted and is removed and, at the same time, in the case where the calcining temperature is not lower than 550° C., the amorphous phase is crystallized, whereby the coating substance becomes an amorphous or crystalline film of calcium phosphate. The coated base is preferably calcined at a temperature of 500° C. to 1000° C. to densify the coating film. When a base material which is apt to deteriorate, e.g., titanium alloy and stainless, is used, the calcining temperature is particularly preferably 500° C. to 800° C. The retention time for calcining is preferably 1 minute to 1 hour in view of productivity. Thus, calcining is carried out in a condition that the coating film is sufficiently densified to obtain sufficient adhesion strength. A means of determining when sufficient calcining has been conducted is as follows. An indenter of Vickers is forced into the coated film. Calcining is taken as completed if there is no peel around the indenter.

In order to obtain a further improved coating film, the rate of temperature increase in the calcination step or a heat treatment step hereinafter described, which may be conducted prior to calcination if desired, is of importance. In particular, until a temperature at which organic matter is burnt and removed is reached, the rate of temperature increase is preferably not more than 5° C./min. If this rate is 7° C./min or higher, a small degree of bubbling occurs on the resulting film. If the rate is 10° C./min or higher, some parts of the surface of the base remain uncoated. This is the basis for limiting the rate of temperature increase until a temperature at which organic matter in the raw material is removed is reached as still another preferred embodiment of the present invention.

The removal of organic matter by combustion may be effected by a heat treating step which is separately conducted prior to calcination, in which the coating film is treated at a temperature lower than the calcining temperature. Where the coating step is repeatedly conducted in order to form a thick film, a series of steps consisting of coating, drying, and the above-mentioned heat treatment are repeated a number of times.

The film forming process according to the present invention has the following advantages:

1) Even when the coating film is calcined at a temperature as low as about 600° to 800° C., a smooth, homogeneous, and dense film free from peeling can be obtained. This is believed to be because the coating material is a uniform gel or solution so that the resulting coating film has an extremely fine structure.
2) Cracks in the film hardly occur. This is believed to be because the chelate compound exhibits a viscous flow at the time of calcination thereby providing a film having a high packing density.
3) The process is easy to carry out, and the raw materials are easy to handle. Expensive raw materials and an exclusive apparatus are not required.
4) Since the preparation of the coating material can be carried out in a solution state, the resulting film has high homogeneity and high purity. The composition of the film is easy to control.
5) Even a base having a complicated shape can be coated with ease. Therefore, a coating film can easily be formed on a high strength base having a shape of hard tissue in a living body to provide a useful substitute for a hard tissue in a living body. Examples of the base having a shape of hard tissue include a stem of artificial joint, and an artificial root.

The present invention is now illustrated in greater detail with reference to the following Examples, but it should be understood that the present invention is not deemed to be limited thereto. Unless otherwise indicated, all the percents are by weight.

EXAMPLE 1

The influence of calcining temperature on the resulting film was evaluated as follows.

In 1 l of distilled water was dissolved $3.125 \times 10^{-2}$ mol of calcium nitrate. An equimolar amount of ammonium ethylenediaminetetraacetate (EDTA) was added to the solution and allowed to react for 30 minutes while stirring. To the reaction mixture was added $1.875 \times 10^{-2}$ mol of ammonium phosphate (giving a total metal molar concentration of 0.05 mol/l), followed by further stirring until the mixture became a clear solution. The solution was ten-fold concentrated at 120° C. and adjusted to pH 4.0 to prepare a coating solution.

A plate of a sintered alumina ceramic was dipped in the coating solution, removed, dried, and heat treated by heating up to 500° C. at a rate of temperature increase of 5° C./min. The operations of dipping through heat treatment were repeated 10 times, and the resulting coated base was calcined at a temperature varying from 500° C. to 1100° C. as shown in Table 1 below to form a film on the surface of the base.

The formed film had a smoothness of a surface roughness Ra of less than 0.06 µm as measured with a surface roughness meter and neither cracks nor peeling was observed under a scanning electron microscope. The crystalline phase obtained by calcining at 550° C. or higher temperatures was found to be a single HAP phase free from an impurity phase such as a reaction product with the base or a decomposition product.

EXAMPLE 2

The influence of pH of a coating solution on the resulting film was evaluated as follows.

A coating solution was prepared in the same manner as in Example 1, except for varying the pH from 6.0 to 12.0 as shown in Table 1. The operations of dip coating through heat treatment were repeated in the same manner as in Example 1, followed by calcination at 600° C.

The formed film had a smoothness of a surface roughness Ra of less than 0.06 µm as measured with a surface roughness meter and neither cracks nor peeling was observed under a scanning electron microscope. The crystalline phase was found to be a single HAP phase free from an impurity phase such as a reaction product with the base or a decomposition product.

EXAMPLE 3

The influence of the total metal molar concentration in the system for preparing a coating solution upon the resulting film was evaluated as follows.

A clear coating solution was prepared in the same manner as in Example 1, except for changing the total metal molar concentration in the preparation system to 0.10, 0.15 or 0.20 mol/l with the Ca/P atomic ratio being fixed at 1.67. The EDTA was added in an amount equimolar to calcium nitrate. Each of the resulting solutions was concentrated at 120° C. to increase its total metal molar concentration to 0.5 mol/l and adjusted to pH 4.0 to prepare a coating solution. A film was formed on a base by using the resulting solution in the same manner as in Example 1.

The formed film had a smoothness of a surface roughness Ra of less than 0.06 µm as measured with a surface roughness meter and neither cracks nor peeling was observed under a scanning electron microscope. The crystalline phase was found to be a single HAP phase free from an impurity phase such as a reaction product with the base or a decomposition product.

EXAMPLE 4

The influence of the rate of temperature increase in the heat treatment upon the resulting film was evaluated as follows.

A coating solution was prepared, and a base was dipped therein and dried in the same manner as in Example 1. The coated base was heat treated by heating up to 500° C. at a varied rate of temperature increase of from 1° to 3° C./min. The operation from dip coating through heat treatment was repeated 10 times, and the coated base was calcined at 600° C. to form a film.

The formed film had a smoothness of a surface roughness Ra of less than 0.06 µm as measured with a surface roughness meter and neither cracks nor peeling was observed under a scanning electron microscope. The crystalline phase was found to be a single HAP phase free from an impurity phase such as a reaction product with the base or a decomposition product.

EXAMPLE 5

In Example 5, the composition of a coating solution used in Example 1 was changed to evaluate its influence on the resulting film.

In 1 l of distilled water was dissolved $3.00 \times 10^{-2}$ mol of calcium nitrate. An equimolar amount of ammonium ethylenediaminetetraacetate (EDTA) was added to the solution and allowed to react for 30 minutes while stirring. To the reaction mixture was added $2.00 \times 10^{-2}$ mol of ammonium phosphate, followed by further stirring until the mixture became a clear solution. The solution was ten-fold concentrated at 120° C. and adjusted to pH 4.0 to prepare a coating solution.

A plate of a sintered alumina ceramic was dipped in the coating solution, removed, dried, and heat treated by heating up to 500° C. at a rate of temperature increase of 5° C./min. The operations of dipping through heat treatment were repeated 10 times, and the resulting coated base was calcined at 600° C. to form a film on the surface of the base.

The formed film had a smoothness of a surface roughness Ra of less than 0.06 µm as measured with a surface roughness meter and neither cracks nor peeling was observed under a scanning electron microscope. The crystalline phase was found to be a single TCP phase free from an impurity phase such as a reaction product with the base or a decomposition product. Based on the fact that the crystalline phase of the film obtained in Examples 1 to 4 was HAP, it can be seen that the crystalline phase of a coating film can be controlled by changing the composition of the coating solution.

EXAMPLE 6

The influence of the material of the base on the film formed thereon was evaluated as follows.

A film was formed on a base in the same manner as in Example 1, except for using a plate of a sintered cubic zirconia ceramic as a base and calcining at 600° C.

The formed film had a smoothness of a surface roughness Ra of less than 0.06 µm as measured with a surface roughness meter and neither cracks nor peeling was observed under a scanning electron microscope. The crystalline phase was found to be a single HAP phase free from an impurity phase such as a reaction product with the base or a decomposition product. Phase transition of the base was not observed. Accordingly, it can be seen that the film and the ceramic base can be closely adhered to each other without interfering with each other.

EXAMPLE 7

The influence of the material of a base on the film formed thereon was evaluated as follows.

A film was formed on a base in the same manner as in Example 1, except for using a plate of a Ti-6Al-4V alloy as a base and calcining at 600° C.

The formed film was smooth, and neither cracks nor peeling was observed under a scanning electron microscope. The crystalline phase of the film was a single HAP phase free from an impurity phase such as a reaction product with the base or a decomposition product. Oxidation of the base was not observed. Accordingly, it can be seen that the film and the metallic base can be closely adhered without interfering with each other.

COMPARATIVE EXAMPLE 1

The importance of a chelating agent in the step of preparing a coating solution was confirmed as follows.

In 1 l of distilled water was dissolved $3.125 \times 10^{-2}$ mol of calcium nitrate. Without adding ammonium ethylenediaminetetraacetate (EDTA), $1.875 \times 10^{-2}$ mol of ammonium phosphate was directly added to the solution, whereupon a precipitate was formed instantaneously, with a uniform coating solution not being obtained.

COMPARATIVE EXAMPLE 2

The importance of pH of a coating solution was confirmed as follows.

A coating solution was prepared in the same manner as in Example 1 and adjusted to a pH of from 3.5;to 2.0, whereupon a precipitate was formed, with a uniform coating solution not being obtained.

COMPARATIVE EXAMPLE 3

The influence of the rate of temperature increase in heat treatment upon the resulting film was evaluated as follows.

A coating solution was prepared in the same manner as in Example 1. A base was dipped therein, removed, dried, and heat treated by heating up to 500° C. at a rate of temperature increase varying from 7° to 20° C./min as shown in Table 1. After repeating the operations of dipping through heat treatment 10 times, the coated base was calcined at 600° C.

Observation of the resulting film under a scanning electron microscope revealed traces of bubbling. On the samples heated at a rate of not less than 10° C./min., some parts of the surface remained uncoated.

COMPARATIVE EXAMPLE 4

The influence of a total metal molar concentration in the system for dissolving the raw materials to prepare a coating solution upon the resulting film was confirmed as follows.

In 1 l of distilled water was dissolved $1.5625 \times 10^{-1}$ mol of calcium nitrate. An equimolar amount of ammonium ethylenediaminetetraacetate (EDTA) was added to the solution and allowed to react for 30 minutes while stirring. To the reaction mixture was added $0.9375 \times 10^{-1}$ mol of ammonium phosphate (giving a total metal molar concentration of 0.25 mol/l), followed by further stirring until the mixture became a clear solution. The solution was two-fold concentrated at 120° C. and adjusted to pH 4.0 to prepare a coating solution.

An alumina plate was dipped in the coating solution, removed, and dried. The coating film was not a transparent gel but was a white turbid gel. The coating film was heat treated by heating up to 500° C. at a rate of temperature increase of 5° C./min. The operations of dipping through heat treatment were repeated 10 times, and the resulting coated base was calcined at 900° C. to form a film on the surface of the base.

The formed film contained CaO as an impurity phase in addition to an HAP phase.

TABLE 1

| Example No. | Run No. | Ca/P Ratio | Base | Coating Solution Concentration 1* (mol/l) | pH | Concentration 2** (mol/l) | State | Rate of Temp. Rise (°C./min) | Calcining*** Temp. (°C.) | Crystalline Phase | Film Properties | Deterioration of Base | Remark |
|---|---|---|---|---|---|---|---|---|---|---|---|---|---|
| 1 | 1 | 1.67 | Al₂O₃ | 0.05 | 4.0 | 0.5 | solution | 5 | 500 | amorphous | smooth | not observed | Invention |
|  | 2 | " | " | " | " | " | " | " | 550 | HAP | " | " | " |
|  | 3 | " | " | " | " | " | " | " | 600 | " | " | " | " |
|  | 4 | " | " | " | " | " | " | " | 900 | " | " | " | " |
|  | 5 | " | " | " | " | " | " | " | 1100 | " | " | " | " |
| 2 | 6 | " | " | " | 6.0 | " | " | " | 600 | " | " | " | " |
|  | 7 | " | " | " | 8.0 | " | " | " | " | " | " | " | " |
|  | 8 | " | " | " | 10.0 | " | " | " | " | " | " | " | " |
|  | 9 | " | " | " | 12.0 | " | " | " | " | " | " | " | " |
| 3 | 10 | " | " | 0.10 | 4.0 | " | " | " | " | " | " | " | " |
|  | 11 | " | " | 0.15 | " | " | " | " | " | " | " | " | " |
|  | 12 | " | " | 0.20 | " | " | " | " | " | " | " | " | " |
| 4 | 13 | " | " | 0.05 | " | " | " | 1 | " | " | " | " | " |
|  | 14 | " | " | " | " | " | " | 3 | " | " | " | " | " |
| 5 | 15 | 1.50 | " | " | " | " | " | 5 | " | TCP | " | " | " |
| 6 | 16 | 1.67 | t-ZrO₂ | " | " | " | " | " | " | HAP | " | " | " |
| 7 | 17 | " | T-6Al-4V | " | " | " | " | " | " | " | " | " | " |
| Compara. 1 | 18 | " | " | " |  |  | precipitate |  |  |  |  |  | Comparison |
| Compara. 2 | 19 | " | " | " | 3.5 |  | precipitate |  |  |  |  |  | " |
|  | 20 | " | " | " | 2.0 |  | precipitate |  |  |  |  |  | " |
| Compara. 3 | 21 | " | Al₂O₃ | " | 4.0 | 0.5 | solution | 7 | 600° C. | HAP | trace of bubbles | not observed | " |
|  | 22 | " | " | " | " | " | " | 10 | " | " | bub- | " | " |

TABLE 1-continued

| | | | | Coating Solution | | | | Calcining*** | | Characteristics | | | |
|---|---|---|---|---|---|---|---|---|---|---|---|---|---|
| | | | | | | | | Rate of | | | | | |
| Example No. | Run No. | Ca/P Ratio | Base | Concentration 1* (mol/l) | pH | Concentration 2** (mol/l) | State | Temp. Rise (°C./min) | Temp. (°C.) | Crystalline Phase | Film Properties | Deterioration of Base | Remark |
| | 23 | " | " | " | " | " | " | 20 | " | " | bling bubbling | " | " |
| Compara. 4 | 24 | " | " | 0.25 | " | " | " | 5 | 900 | CaO-containing | | " | " |

Note:
*Total metal (Ca + P) molar concentration in the system for dissolving the raw materials.
**Total metal (Ca + P) molar concentration of a concentrated coating solution.
***In calcining, the rate of temperature rise represents the rate of temperature rise in heat treating and the temperature means the calcining temperature.

As described and demonstrated above, a high purity calcium phosphate coating film can easily be formed on the surface of various high strength bases by the process of the present invention. High strength bases having a calcium phosphate coating film thus formed thereon have high bioaffinity and are useful as artificial bones or artificial dental roots.

While the invention has been described in detail and with reference to specific examples thereof, it will be apparent to one skilled in the art that various changes and modifications can be made therein without departing from the spirit and scope thereof.

What is claimed is:

1. A process for producing a calcium phosphate coating film comprising (1) dissolving (a) a salt containing phosphorus, a salt containing calcium, and a chelating agent capable of coordinating to either one or both of the metallic ions of these salts or (b) a chelate compound containing at least one of phosphorus and calcium and a salt containing the other in a solvent to prepare a sediment-free coating solution, (2) coating a base with the coating solution, (3) drying the coated base, and (4) calcining the coated base.

2. A process as claimed in claim 1, wherein said chelating agent is ethylenediaminetetraacetic acid compound.

3. A process as claimed in claim 1, wherein said coating solution has a pH of not lower than 4.0.

4. A process as claimed in claim 1, wherein the coating solution has a total metal molar concentration of 0.2 mol/l or less.

5. A process as claimed in claim 1, wherein said calcining step is carried out at an increasing temperature rate of 5° C./min or less until a temperature is reached where any organic matter in (a) or (b) is combusted and removed.

6. A process as claimed in claim 1, wherein, prior to said calcining step, said process further comprises heat treating said coated base at an increasing temperature rate of 5° C./min or less.

7. A process for producing a substitute for hard tissue in a living body which comprises (1) dissolving (a) a salt containing phosphorus, a salt containing calcium, and a chelating agent capable of coordinating to either one or both of the metallic ions of these salts or (b) a chelate compound containing at least one of phosphorus and calcium and a salt containing the other in a solvent to prepare a sediment-free coating solution, (2) coating a base with the coating solution, (3) drying the coated base, and (4) calcining the coated base to form a calcium phosphate coating film on the surface of said base.

8. A process as claimed in claim 7, wherein said base is in the shape of a bone, a dental root or a joint.

* * * * *